United States Patent
Stotland et al.

(10) Patent No.: US 9,662,043 B1
(45) Date of Patent: May 30, 2017

(54) GAUGE FOR DETERMINING NOSTRIL DEFORMITY AND METHOD FOR USING THE SAME

(75) Inventors: Mitchell A. Stotland, Norwich, VT (US); Steven D. Reinitz, Wyckoff, NJ (US)

(73) Assignee: DARTMOUTH-HITCHCOCK CLINIC, Lebanon, NH (US)

( * ) Notice: Subject to any disclaimer, the term of this patent is extended or adjusted under 35 U.S.C. 154(b) by 928 days.

(21) Appl. No.: 13/050,033

(22) Filed: Mar. 17, 2011

Related U.S. Application Data

(60) Provisional application No. 61/319,942, filed on Apr. 1, 2010.

(51) Int. Cl.
*A61B 5/107* (2006.01)
*A61B 17/24* (2006.01)
*G01B 3/34* (2006.01)

(52) U.S. Cl.
CPC ............ *A61B 5/1076* (2013.01); *A61B 17/24* (2013.01)

(58) Field of Classification Search
CPC .............................. A61B 5/1076; A61B 17/24
USPC ........ 600/587, 199; 33/511, 512, 542, 555.1
See application file for complete search history.

(56) References Cited

U.S. PATENT DOCUMENTS

| | | | |
|---|---|---|---|
| 146,974 A | 2/1874 | Allen | |
| 1,774,084 A * | 8/1930 | Cooney ................... | E21B 10/02 175/391 |
| 2,767,478 A * | 10/1956 | Adams ....................... | 33/501.05 |
| 3,720,273 A * | 3/1973 | McKenry ................ | E21B 10/44 175/335 |
| 3,830,321 A * | 8/1974 | McKenry ................ | E21B 10/02 175/332 |
| 4,107,850 A * | 8/1978 | Adler .............................. | 33/542 |
| 4,170,069 A * | 10/1979 | Katsanevas ................. | 33/199 R |
| 4,211,241 A * | 7/1980 | Kaster et al. ................. | 600/587 |
| 4,216,586 A | 8/1980 | Long | |

(Continued)

*Primary Examiner* — Sean Dougherty
(74) *Attorney, Agent, or Firm* — Loginov & Associates; William A. Loginov

(57) ABSTRACT

This invention provides a novel nostril gauge system and methods for using the same, which allows the practitioner to measure the size of deformed nostrils resulting from any cause such as from a cleft lip and/or cleft palate, a traumatic injury, an infectious process, a prior surgical intervention, etc. The device allows for the expeditious and accurate measurement of the size/caliber of normal and deformed nostrils before any type of nasal reconstruction intended to correct asymmetric nostril openings (nares). The gauge includes a series of measured and accurately sized gauge steps that are readily used and result in a more precise nostril sizing. The gauge includes a plurality of spines, each having steps thereon correlating to different circumferential sizes. The gauge system is provided with printed size indicia that refers to each gauge step and facilitates the measuring process. In illustrative embodiments, the gauge body defines a loop with a plurality of gauge spines, arranged around its perimeter. The axial depth of every gauge step is sufficient to adequately engage the nostril during sizing. Every step can be identified by indicium that is correlated to that particular diameter. In another embodiment, the spines can be mounted orthogonally at the ends of arms arranged like spokes of a wheel about the perimeter of a body.

11 Claims, 13 Drawing Sheets

(56) References Cited

U.S. PATENT DOCUMENTS

| | | | | |
|---|---|---|---|---|
| 4,414,977 | A * | 11/1983 | Rezakhany | 606/199 |
| 4,493,595 | A * | 1/1985 | Klein | B23B 39/161 |
| | | | | 279/103 |
| D342,684 | S * | 12/1993 | Halo | D10/64 |
| 5,336,163 | A | 8/1994 | DeMane et al. | |
| 5,497,843 | A * | 3/1996 | Burns | E21C 35/183 |
| | | | | 175/403 |
| 6,004,342 | A * | 12/1999 | Filis | 606/199 |
| 6,106,541 | A | 8/2000 | Hurbis | |
| 6,270,512 | B1 * | 8/2001 | Rittmann | 606/199 |
| 6,540,766 | B2 * | 4/2003 | Martino | 606/199 |
| 6,761,693 | B1 | 7/2004 | Rasmussen | |
| 6,863,066 | B2 * | 3/2005 | Ogle | 128/200.24 |
| 6,931,744 | B1 * | 8/2005 | Ikerd et al. | 33/501.45 |
| 6,971,388 | B1 * | 12/2005 | Michaels | 128/206.11 |
| 7,694,428 | B2 * | 4/2010 | Cannon | G01B 5/0023 |
| | | | | 33/1 BB |
| 7,727,252 | B2 * | 6/2010 | Maryanka | 606/199 |
| 7,740,643 | B2 * | 6/2010 | Maryanka | 606/199 |
| 7,856,979 | B2 * | 12/2010 | Doshi et al. | 128/206.11 |
| 7,998,093 | B2 * | 8/2011 | MacDonald | 600/587 |
| 8,038,712 | B2 * | 10/2011 | van der Burg et al. | 623/10 |
| 8,047,201 | B2 * | 11/2011 | Guyuron et al. | 128/200.24 |
| D652,144 | S * | 1/2012 | Stotland et al. | D24/140 |
| 8,225,796 | B2 * | 7/2012 | Davenport et al. | 128/207.18 |
| 8,365,736 | B2 * | 2/2013 | Doshi et al. | 128/207.18 |
| 8,376,743 | B1 * | 2/2013 | Bukhary | 433/140 |
| 8,459,254 | B1 * | 6/2013 | Jassir et al. | 128/200.24 |
| 2001/0011421 | A1 * | 8/2001 | Bakke | G01B 3/34 |
| | | | | 33/501.45 |
| 2004/0059368 | A1 * | 3/2004 | Maryanka | 606/191 |
| 2004/0147954 | A1 * | 7/2004 | Wood | 606/199 |
| 2004/0237967 | A1 * | 12/2004 | Davis | 128/207.18 |
| 2005/0199248 | A1 * | 9/2005 | Pflueger et al. | 128/848 |
| 2005/0235505 | A1 * | 10/2005 | Joseph | G01B 3/34 |
| | | | | 33/501.45 |
| 2006/0047226 | A1 * | 3/2006 | Wood | 600/587 |
| 2006/0090362 | A1 * | 5/2006 | Wood | 33/512 |
| 2006/0259064 | A1 * | 11/2006 | Maryanka | 606/199 |
| 2008/0269643 | A1 | 10/2008 | Morriss | |
| 2008/0276475 | A1 * | 11/2008 | Schafer | G01B 3/34 |
| | | | | 33/501.45 |
| 2009/0062694 | A1 * | 3/2009 | MacDonald | 600/587 |
| 2009/0250066 | A1 | 10/2009 | Daly | |
| 2010/0000550 | A1 * | 1/2010 | Pflueger et al. | 128/848 |
| 2010/0319709 | A1 * | 12/2010 | Goncalves | 128/848 |

* cited by examiner

GAUGE FOR DETERMINING NOSTRIL DEFORMITY AND METHOD FOR USING THE SAME

RELATED APPLICATION

This application claims the benefit of U.S. Provisional Application Ser. No. 61/319,942, filed Apr. 1, 2010, entitled GAUGE FOR DETERMINING NOSTRIL DEFORMITY AND METHOD FOR USING THE SAME, the entire disclosure of which is herein incorporated by reference.

FIELD OF THE INVENTION

This invention relates to devices to facilitate the accurate gauging of the size/caliber of deformed nostrils resulting from any cause such as from a cleft lip and/or cleft palate, a traumatic injury, an infectious process, a prior surgical intervention, etc. The device allows for the expeditious and accurate measurement of the size/caliber of normal and deformed nostrils before any type of nasal reconstruction intended to correct asymmetric nostril openings (nares).

BACKGROUND OF THE INVENTION

Cleft lips and palates are a birth defect that occurs once in approximately 600-800 live births in the United States. The highest prevalence rates for cleft lip and palate are reported for Asians and Native Americans, with Africans having the lowest rate. This birth defect forms in the first six to eight weeks of pregnancy when the embryo's head and face take shape. The embryo's face and head are formed by the joining of several convergent growing tissues. Sometimes, the tissues fail to meet or fuse and a gap (cleft) results.

A child born with a cleft lip and/or palate has a significant problem with forming a suction, which in turn impedes feeding the infant. The defect is noticeable and can take the form of an incomplete unilateral gap, which does not pass far beyond the lip, a complete unilateral cleft, which extends into the nose, or a bilateral complete cleft that extends upwards into both nostrils. The cleft can affect the underlying muscle and bone tissue. The deformity may continue from the lip back to the palate or from the rear of the palate forward. The cleft lip and/or palate can be remediated surgically through a series of one or more procedures over a period of several years. The program of reconstruction usually begins with closure of the lip in the early weeks/months of life, the palate repair closer to 10-12 months of age, followed by orthodontic procedures and occasional supplemental surgical interventions for appearance, speech or other related issues. These procedures are conducted over a series of years as the child grows and develops.

The surgical closure of the cleft lip can result in a size difference between the two nostrils and deformity of the nose. Typically, the nostril on the cleft side in a unilateral incomplete or complete cleft has been splayed laterally and has an abnormal shape and caliber (the nostril is typically larger). In a bilateral complete cleft lip, both sides tend to be splayed laterally and are abnormally large.

A major challenge in the reconstruction of cleft lip deformity is the characteristic nasal distortion that is present at birth. The discrepancy in the internal nostril caliber is a particularly important component of the cleft-related nasal distortion. In the unilateral cleft lip, the cleft surgeon's objective is to match the caliber of the normal non-cleft side nostril with the abnormal cleft side nostril. In the case of a bilateral cleft lip, the objective is to create complete nostril rings that are appropriately sized for the patient's nose and face.

Cleft nostril asymmetry is caused by a number of factors. The first cause is the congenital absence of an intact orbicularis oris sphincter muscle that results in the lateral splaying of the columella and cleft-side alar base in opposing directions. The orbicularis oris sphincter is the muscle that surrounds the opening of the mouth and allows the puckering of the lips and closes the mouth. The columella is the fleshy external end of the nasal septum that sits between the two nostrils. The ala refers to the cartilage that surrounds the nostrils. Each of the nostrils is defined by a cartilage structure surrounded by layers of epidermis, one on the outside and one on the inside. The opening of the nostrils is a ring of skin that has a slightly raised feature along the bottom of the nostril, which is also referred to as the 'sill'. The second cause of nostril asymmetry is a congenital enlargement of the internal caliber of the cleft side nostril. This is seen in incomplete unilateral clefts as well. The third factor contributing to nostril asymmetry is the associated distortion in the underlying cartilage as well as the dento-maxillary (upper jaw) support structure which can reveal anything between a small step-deformity to a large alveolar ridge (gumline) cleft.

The reconstructive cleft surgeon's goal is to produce a balanced nose having nostrils that are laterally symmetric and equal in nostril caliber. Cleft surgeons are frequently confronted by older children, teenagers and young adults whose nostril size discrepancy represents a major component of their secondary deformity. These deformities may produce significant psychological and social problems, especially at a time when personal appearance, self-esteem and confidence are growing. Therefore, it is desirable to produce a set of nostrils that are equal in caliber and balanced to the eye.

The cleft surgeon first closes the cleft lip by incising tissue around the borders of the cleft and then mobilizing the skin, muscle and lining of the lip and nose together. When operating on the nose, it is common to mobilize the outer skin and the underlying mucosal lining off the alar cartilage in order to allow the cartilage to unbuckle from its previously abnormal configuration. The upper lip is generally shorter along the cleft side (measured along a cephalad-caudad orientation; that is, head-to-toe orientation). It is therefore necessary to lengthen the upper lip simultaneous to the reconstruction of the cleft-side of the nose. It is generally necessary for the surgeon to remove a portion of skin along the nostril floor, in the axis of the cleft, to facilitate appropriate repair and correct the caliber mismatch between the two nares. The nostrils are thus repositioned and re-anchored. The problem with incorrectly balancing the nostril shape and caliber is that one of the nostrils may subsequently be noticeably smaller or larger, necessitating further surgery. This is a commonly encountered problem.

Determining the equalization of the nostrils and their calibers has traditionally been performed by the surgeon visually approximating ('eyeballing') the sizes and shapes. In recent years, Dr. Stotland has begun to use urethral dilators in order to gauge the relative internal caliber of the non-cleft versus the cleft nostril. These instruments resemble traditional knitting needles and feature long shafts with a tapered end. The dilators are commonly used for urological procedures and are available in a variety of sizes. Typically, the dilators are not marked in circumferential diameters and are not purposefully designed for this particular use. Being able to accurately determine the difference in internal circumference of the two nares would allow the surgeon to precisely correct any measured discrepancy by removing or adding tissue, as required.

FIG. 1 is a view 100 in which a nasal reconstruction patient 102 is presented, according to the prior art. This illustrative patient has a congenital unilateral cleft lip that was closed by surgery as an infant, leaving a post-surgical lip deformity 104, a scar on the upper lip 106 and a nose 108 that has a normal non-cleft side nostril 110 and an abnormal cleft-side nostril 112. The cleft-side nostril is likewise deformed and pulled towards the cheek on the cleft side. The patient has an intubation tube 116 inserted in the mouth 118. The cleft surgeon or other authorized practitioner (not shown) is attempting to gauge the caliber of each nostril in order to aid in the planning of reconstructive surgery. The cleft surgeon is preparing to insert a typical urethral dilator 120 into the non-cleft side nostril 110 for the purpose of determining the caliber of that nostril. The tissue of the nostril is elastic and tends to form a circle around an inserted object and thereby provides a shape that has a measurable circumference that yields the caliber of the nostril.

FIG. 2 is a view 200 of the cleft surgeon (not shown) determining the gauge of the normal nostril 110, which is the non-cleft side of the nose 108 by inserting a urethral dilator 120 into that nostril, according to the prior art. The cleft surgeon now determines that this particular size of the urethral dilator 120 is correct and notes the measurement of the dilator using a caliper or some other measuring device. It may require retrieval and reinsertion of multiple dilators of different sizes until the correct size is selected. The cleft surgeon now estimates the approximate size of the abnormal, cleft-side nostril 112 and selects the appropriate urethral dilator.

FIG. 3 is a view 300 of the gauging of the caliber of the cleft side nostril 112 of a patient 102 utilizing a urethral dilator 302, according to the prior art. Once the cleft surgeon has withdrawn the urethral dilator 302, a measurement will be taken using a silk suture wrapped around the dilator and then the length of the suture is measured, thereby giving the caliber of the abnormal cleft-side nostril 112. The cleft surgeon will then note the difference between the measurements of the normal nostril 110 and the abnormal nostril 112 in order to determine how much tissue needs to be removed in order to balance and equalize the nostril calibers of the nose 108. Again, it may require retrieval and reinsertion of multiple dilators of different sizes until the correct size is selected.

The traditional methods of 'eye balling' the size of the nostrils and the use of dilators have produced inexact and imperfect results. In addition, these approaches have sometimes resulted in the need for future reconstructive surgery to correct the undesired results.

It is thus desirable to provide for the effective and exact sizing of the nostrils and thereby improve the accuracy and aesthetic outcome of the surgical intervention and hopefully lessen the need for future surgeries, the time/cost of those surgeries and the risks attendant with those surgeries. It is further desirable to have a system and method to measure the caliber of the nostrils before the reconstructive surgery, for determining the amount of tissue to be removed for equalization, and after the surgery, to accurately confirm the results. Moreover, is desirable for the system and method to be able to confront size differentials and provide a process for determining how much tissue needs to be removed from the abnormally sized nostril. It is also desirable to avoid the need for switching out of a plurality of loose gauges or tools that consume time and add clutter and complexity to the procedure. Likewise, it is also desirable to avoid guesses and the improvised use of instruments not intended for this purpose. This device should be applicable not only to nostril asymmetry associated with cleft lip and/or palate, but to any reconstructive challenge involving nares discrepancy such as post-traumatic, post-infectious, post-surgical, non-cleft congenital, etc.

SUMMARY OF THE INVENTION

This invention overcomes the disadvantages of the prior art by providing a novel nostril gauge system and methods for using the same, which allows the practitioner to measure the nostril in an expeditious and accurate manner. The gauge includes a series of measured and accurately sized gauge steps that are readily used and result in a more precise nostril sizing. The gauge system includes a plurality of gauge spines, each of which has several different gauge steps that correlate with different circumferential sizes. The gauge spines are arranged to provide easy insertion and re-insertion. The gauge system is provided with printed size indicia that refers to each gauge step and facilitates the measuring process. In illustrative embodiments, the gauge body defines a loop with a plurality of the gauge spines, arranged around its perimeter. In another embodiment, the spines can be mounted orthogonally at the ends of arms arranged like spokes of a wheel about the perimeter of a body.

The axial depth of every gauge step is sufficient to adequately engage the nostril during sizing. Each step can be identified by color-coded or inscribed indicium that is correlated to that particular diameter. Sizes can be repeated on two or more spines where appropriate, and/or the arrangement of sizes can be interspersed through several spines (i.e., one spine can contain sizes 1, 3, 5 while another contains sizes 2, 4, 6).

In various embodiments, the sizes can be adapted to a particular age or size of the patient, for example, an adult-sized gauge and a children's gauge. The gauge can include any number of the spines, for example, 3, 4, 6 or 8 spines. The base can be a ringed loop with an open center for ease of gripping and manipulation or a simple, fixed intersecting joint. The spines can be radially mounted on the base or offset from the radii eminately from the base centroid. The gauge can be constructed of an approved polymer, metal, ceramic, glass or combination thereof. It is typically constructed to be reusable by applying appropriate sterilization processes.

In a further embodiment, the gauge can comprise one or more shafts that define a straight shaft, curved shaft, rectilinear shaft or an s-shape. Theses shafts can include a plurality of gauge steps incrementally on or both ends.

More particularly, in illustrative embodiments, a gauge for determining a perimeter dimension of an orifice in a body comprises a gauge body constructed and arranged to allow grasping by a user. A plurality of gauge spines are mounted about a perimeter of the gauge body. Each of the gauge spines including a plurality of gauge steps arranged proximally-to-distally in successively smaller diameters, at least one of the spines including at least one gauge step differing in diameter from the gauge steps of another of the spines. The gauge body comprises a ring having an open center. The gauge body is provided with the spines that are each oriented to extend proximally-to-distally along radial lines with respect to a centroid of the gauge body. The gauge body can be provided with spines that are each oriented to extend proximally-to-distally in a location offset from a radius with respect to a centroid of the gauge body. The gauge can also be provided with indicia associated with at least some of the gauge steps each defining the diameter of one of the steps. In an embodiment, the body orifice is a nostril and the diameter of each of the gauge steps defines a diameter of a nostril of predetermined inner perimeter size In another embodiment, a gauge for determining a perimeter dimension of an orifice in a body includes a gauge body constructed and arranged to allow grasping by a user; and a plurality of gauge arms mounted about a perimeter of the gauge body at a proximal end thereof. Each of the gauge arms is interconnected at a distal end to at least one of a plurality of gauge spines, the gauge spines being constructed and arranged to engage the orifice with a given diameter. At least some of the gauge spines differ in diameter from other gauge spines so as to provide a usable range of spine sizes for use in gauging the proper size of the orifice during a reconstructive surgical procedure. At least some of the gauge arms can illustratively include a pair of the gauge spines arranged in a counterpoised relationship with respect to each other and extending along an axis transverse (e.g. a right angle) to an axis of extension of the respective of the gauge arms interconnected therewith. The gauge spines can be parallel to each other, and the gauge body can include an open center to enhance grasping thereof. The gauge can also include indicia located with respect to at least some of the gauge spines indicating the diameter of the respective of the gauge spines. These indicia can be on the spines, the arms and/or the body. The axes of the arms illustratively reside in a plane that also includes the gauge body. The arms are arranged about a perimeter of the body like spokes of a wheel, at approximately equal angular spacing therebetween. In an embodiment, at least some of the gauge arms (and optionally, other portions of the gauge) can be constructed from a flexible material so that the gauge arms constructed from the flexible material can be elastically deformed away from a predetermined of the gauge spines (that is currently in use) so as to be free of interference therewith during use.

In a further embodiment, a medical treatment procedure for sizing a body orifice during reconstructive surgery includes the steps of providing a gauge body constructed and arranged to allow grasping by a user and a plurality of gauge spines mounted about a perimeter of the gauge body. Each of the gauge spines includes a plurality of gauge steps arranged proximally-to-distally in successively smaller diameters. At least one of the spines includes at least one gauge step differing in diameter from the gauge steps of another of the spines and determining a first candidate diameter with respect to one of the gauge steps that corresponds approximately to the inner circumferential diameter of the orifice. The procedure further includes inserting the one of the gauge spines including the gauge step having the candidate diameter and determining if the candidate diameter is correct. If the first candidate diameter is not correct, repeating the selection steps each time with a gauge step defining a second through nth candidate diameter until the respective second through nth candidate diameter is correct; and then determining the size of the measured orifice. Following measurements, a reconstructive surgical procedure is performed on the orifice based upon the correct diameter. The orifice described above can be a nostril and the sizing of the nostril is part of a nasal reconstructive surgery. The above steps can be performed to determine the correct size of a nostril not undergoing the surgery (at least at that time) and used to derive a diameter comparison with the current size of the nostril undergoing the surgery. The comparison is used to determine the amount of material to be excised from the nostril.

BRIEF DESCRIPTION OF THE DRAWINGS

The invention description below refers to the accompanying drawings, of which.

DETAILED DESCRIPTION

Figure 1:
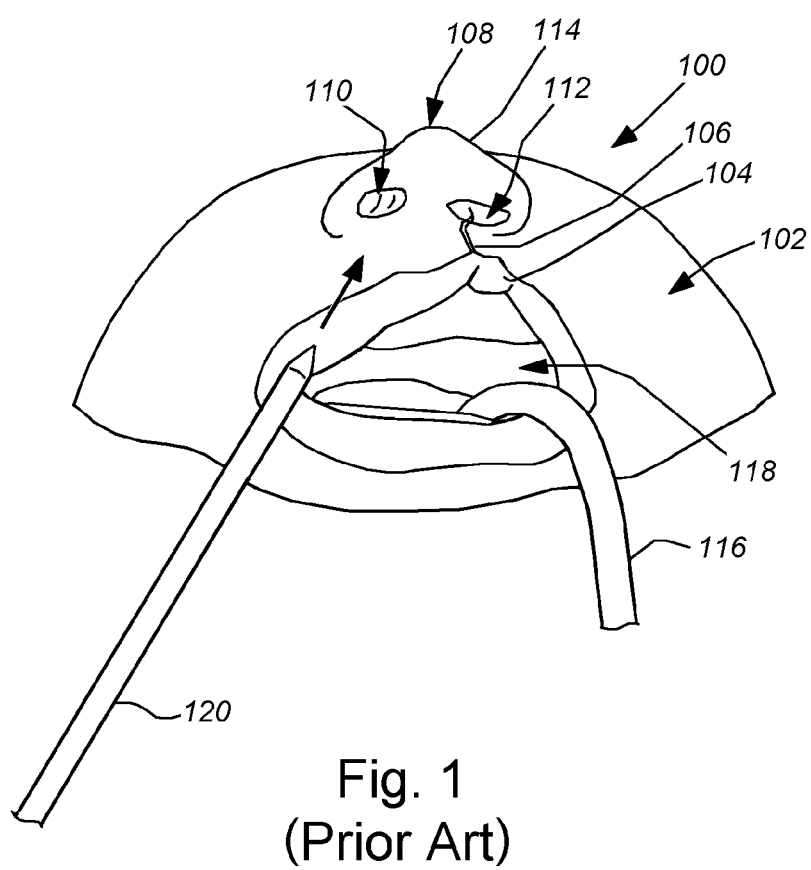
FIG. 1, already described, is a frontal perspective view of a patient about to undergo nostril gauging utilizing a urethral dilator in preparation for nasal reconstruction to correct post-cleft surgery deformity according to the prior art.
Figure 2:
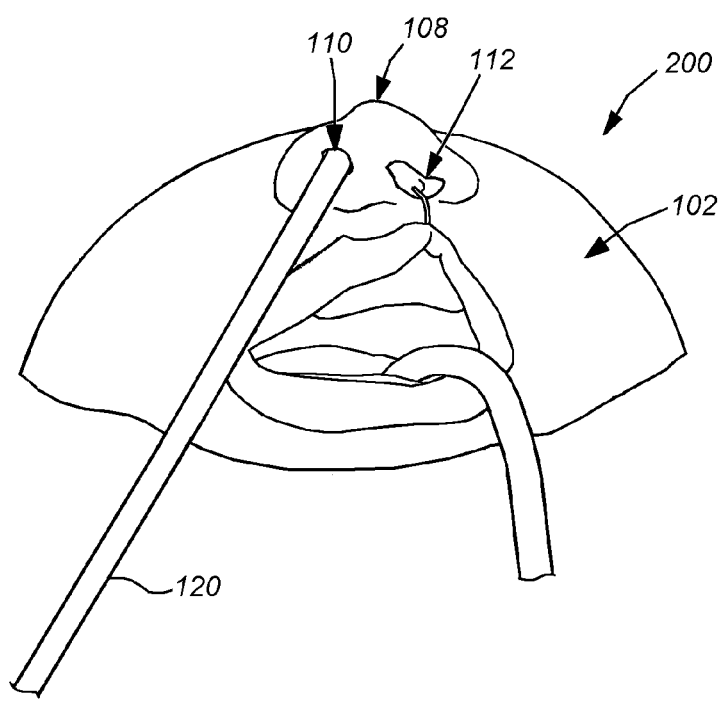
FIG. 2, already described, is a frontal perspective view of a patient undergoing nostril gauging of the normal non-cleft side nostril utilizing a urethral dilator in preparation for nasal reconstruction to correct post-cleft surgery deformity according to the prior art.
Figure 3:
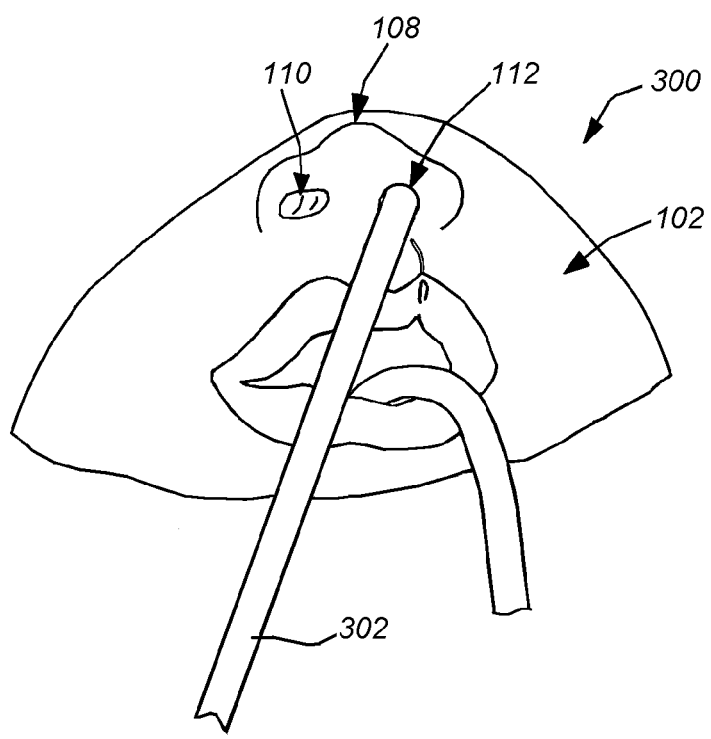
FIG. 3, already described, is a frontal perspective view of a patient undergoing nostril gauging of the abnormal, cleft side nostril utilizing a urethral dilator in preparation for nasal reconstruction to correct post-cleft surgery deformity according to the prior art.
Figure 4:
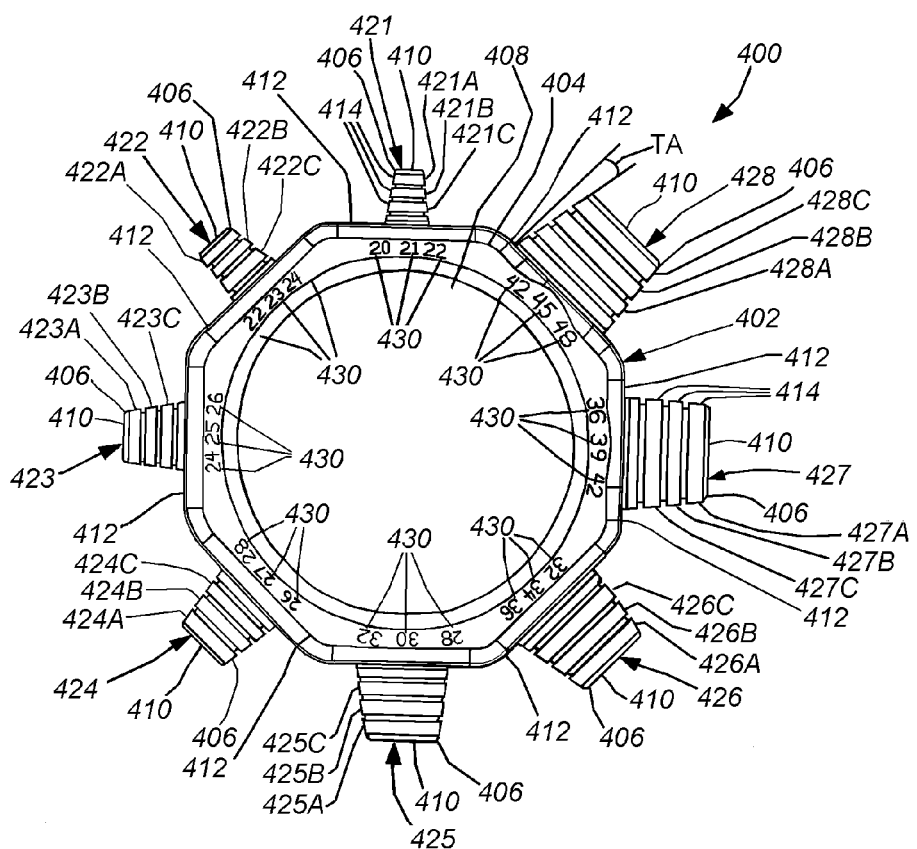
FIG. 4 is a frontal view of the illustrative nostril gauge, detailing various features according to an illustrative embodiment.

FIG. 4 is a frontal view 400 of an illustrative gauge for determining nostril deformity 402 according to an illustrative embodiment. The shape of the illustrative nostril gauge 402 is octagonal, with an octagonal gauge body 404 and eight measurement gauge spines 406. The gauge body 404 is a loop and has a center cutout hole 408 which is provided to reduce the weight, as well as providing a gripping feature for the cleft surgeon. The center cutout hole is approximately 1 inch in diameter. The overall size of the nostril gauge 402 is between 1.5 and 3 inches in diameter for use with children, from the outer surface 410 of one opposing gauge spine 406 to the other opposite gauge spine 406. It is contemplated that an adult size nostril gauge can be up to approximately 7 inches in diameter. While the illustrative gauge spine is depicted as having eight spines, it can be alternatively provided with more or less gauge spines, up to the limit of the ability to employ a gauge spine in nostril measurement without having its insertion into a nostril impeded or impinged upon by adjacent gauge spines. In this embodiment, the spines are oriented to extend proximally-to-distally along radii (radially) with respect to a centroid of the gauge body. As described below, the spines can be radially offset in other embodiments.

The gauge body 404 and gauge spines 406 are composed of a lightweight material, preferably a polymer that is lightweight, biocompatible, autoclavible and approved for operating room use. An illustrative material for the gauge 402 is the polymer Delrin®. The gauge can alternatively be composed of another approved polymer, metal, ceramic, glass or combination of such materials, or another material that is biocompatible, approved for medical use and autoclavible.

The illustrative nostril gauge has one spine 406 centered laterally on each facet 412 of the octagonal gauge body 404. The nostril gauge 402 depicted in FIG. 4 has eight gauge spines 406. Each spine 406 varies in its axial length between approximately 13 to 17 millimeters. On the illustrative nostril gauge the wider spines are longer than the narrower spines. Alternatively, the gauge spines can be longer or shorter, as desired, provided that they are visually discernable and do not over penetrate the patient's nostril. Each gauge spine has stepped gauge rings 414, ranging proximally-to-distally, of three difference sizes and are formed from a continuous taper with annular detents to differentiate between each gauge step. In the illustrative embodiment, each of the step rings 414 is between approximately 2 to 4 millimeters in axial length and varies in its caliber. In alternate embodiments it is expressly contemplated that the steps can be straight cylinders rather than the depicted frustoconical steps. Likewise, the axial length of each inter-step detent is highly variable. Alternatively, the gauge spine can be provided with more or fewer gauge steps. The axial depth of every gauge step is sufficient to adequately engage the nostril during sizing. Every step can be identified by a color-coded or inscribed indicia that is correlated to that particular diameter. Sizes can be repeated on two or more spines where appropriate, and/or the arrangement of sizes can be interspersed through several spines (i.e., one spine can contain sizes 1, 3, 5 while another contains sizes 2, 4, 6).

The gauge spine is constructed that it has the exact same angle of TA, which is desirably approximately 82.75 degrees. In this respect, each gauge spine 406 is circular in its profile and describes the base of a segmented cone.

While it is expressly contemplated that the particular dimensions and size variations between gauge spines and gauge steps is highly variable, the following is a general description of an embodiment by way of example. Gauge spine 421 has three gauge steps 421A, 421B and 421C, each of which has a different size. The illustrative gauge spine 421 is the smallest of the spines and conforms to the lower end of the size of infant nostrils. The circumference of the distal gauge step 421A is approximately 20 millimeters. The circumference of the medial gauge spine 421B is approximately 21 millimeters. The proximal gauge step 421C has a circumference of approximately 22 millimeters. The illustrative gauge spine 422 is furnished with three gauge steps 422A, 422B and 422C. The circumference of gauge step 422A is approximately 22 millimeters. The circumference of gauge step 422B is approximately 23 millimeters. The circumference of gauge step 422C is approximately 24 millimeters. The illustrative gauge spine 423 is furnished with three gauge steps 423A, 423B and 423C. The circumference of gauge step 423A is approximately 24 millimeters. The circumference of gauge step 423B is approximately 25 millimeters. The circumference of gauge step 423C is approximately 26 millimeters. The illustrative gauge spine 424 is furnished with three gauge steps, 424A, 424B and 424C. The circumference of gauge step 424A is approximately 26 millimeters. The circumference of gauge step 424B is approximately 27 millimeters. The circumference of gauge step 424C is approximately 28 millimeters. The illustrative gauge spine 425 is furnished with three gauge steps, 425A, 425B and 425C. The circumference of gauge step 4245 is approximately 28 millimeters. The circumference of gauge step 425B is approximately 30 millimeters. The circumference of gauge step 425C is approximately 32 millimeters. The illustrative gauge spine 426 is furnished with three gauge steps, 426A, 426B and 426C. The circumference of gauge step 426A is approximately 32 millimeters. The circumference of gauge step 426B is approximately 34 millimeters. The circumference of gauge step 426C is approximately 36 millimeters. The illustrative gauge spine 427 is furnished with three gauge steps, 427A, 427B and 427C. The circumference of gauge step 427A is approximately 36 millimeters. The circumference of gauge step 427B is approximately 39 millimeters. The circumference of gauge step 427C is approximately 42 millimeters. The illustrative gauge spine 428 is furnished with three gauge steps, 428A, 428B and 428C. The circumference of gauge step 428A is approximately 42 millimeters. The circumference of gauge step 428B is approximately 45 millimeters. The circumference of gauge step 428C is approximately 48 millimeters. It should be clear that a gauge directed specifically towards an adult-sized patient can provide a larger variation between gauge step sizes on a particular gauge spine. Conversely, an infant and/or juvenile nostril gauge will desirably recommend a smaller variation in increments of the gauge sizes on a particular gauge spine. Generally, a smaller nostril requires more precision in sizing measurements to assure proper balance with respect to the normal, non-cleft side nostril, thereby achieving the desired surgical outcome.

The gauge body 404 can be furnished with indicia 430 that relate to each of the particular gauge steps 414 on a respective gauge spine 406. The indicia 430 provide the cleft surgeon with a visual cue and expedite the correct reading of the caliber of a particular nostril. Notably, this attains a faster and more accurate measurement procedure than the urethral dilators 120 and 302 of the prior art. This in turn leads to a more predictable outcome in the nasal reconstruction. The employment of the nostril gauge 402 in a reconstructive surgical procedure will be explained more particularly below.

Figure 5:
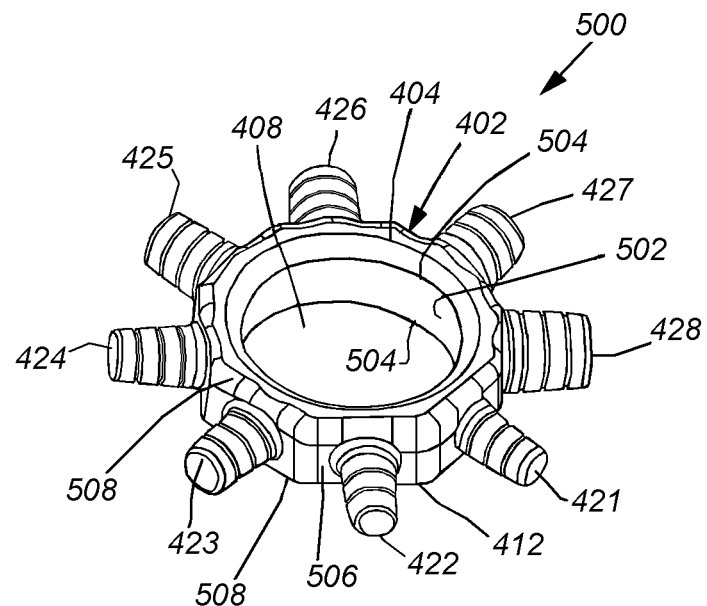
FIG. 5 is a frontal perspective view of the illustrative nostril gauge, detailing various features according to an illustrative embodiment.

FIG. 5 is a frontal perspective view 500 of the illustrative nostril gauge 402 having a gauge body 404, gauge spines 421-428 and a center hole 408. The inner wall 502 is cylindrical with rounded over edges 504 on each of the opposing sides. The outer wall 506 describes a flat surface with a rounded over edge 508 at the outside. The purpose of the rounded over surfaces 508 and 504 is to enhance cleaning and avoid any sharp lines that might injure the patient or cleft surgeon while the gauging is being conducted.

Figure 6:
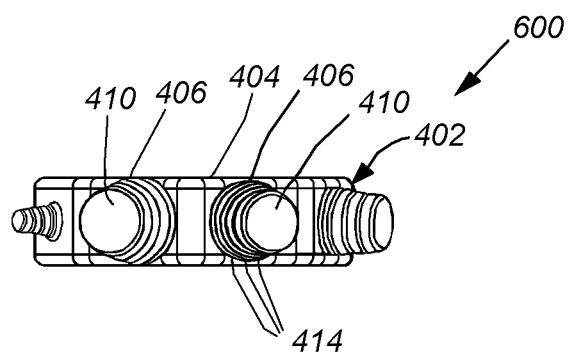
FIG. 6 is an end on view of the illustrative nostril gauge, detailing various features according to an illustrative embodiment.

FIG. 6 is an end-on view 600 of the illustrative octagonal nostril gauge 402. Each gauge spine 406 is described by a flat end surface 410 and has a circular profile, as previously noted. The respective gauge steps 414 are shown and proceed from the narrowest gauge steps at the outer surface 410 to the base of the gauge spine where it meets the body of the gauge spine 404.

Figure 7:
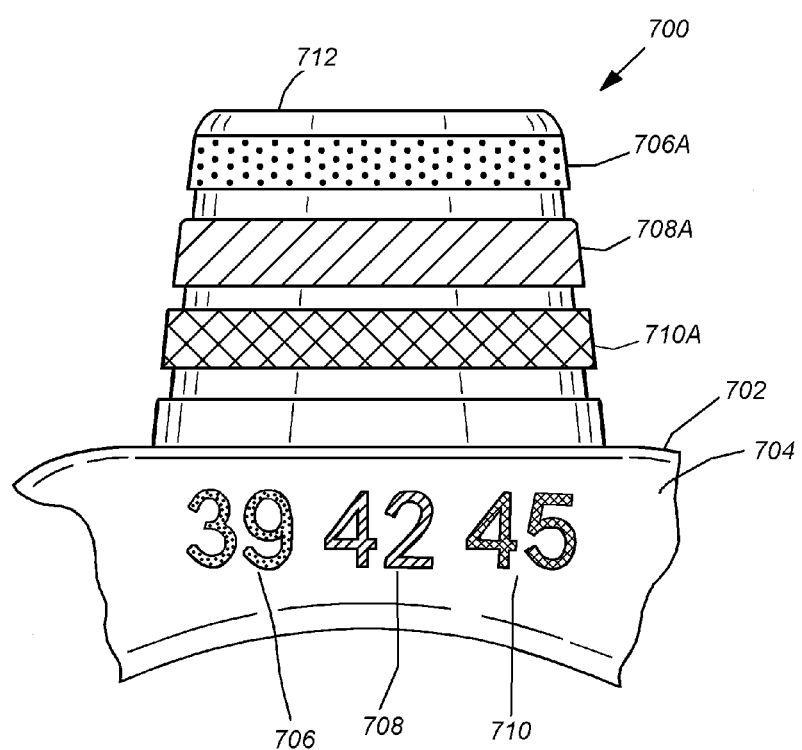
FIG. 7 is a close up frontal view of a portion of the illustrative nostril gauge, detailing various features according to an illustrative embodiment.

In an alternate embodiment, FIG. 7 is a close up view 700 of a segment of the illustrative octagonal nostril gauge 702, displaying a portion of the gauge body 704 on which are inscribed three measurement indicia 706, 708 and 710. Each of the indicia 706, 708 and 710 relate to a gauge step on the respective gauge spine 712. In this alternate embodiment, the three illustrative gauge steps are color-coded and each of the corresponding indicia is coded to match the related gauge step. The color-coding expedites measurement. It is contemplated that the colors are presented in distinctive shades, for example, black, green and red; black, white and red or some other combination of colors that visually distinguishes between the differing gauge steps. It is further contemplated that the colors are coded so as to avoid mistake by people having the common varieties of color blindness. In the illustrative nostril body 702, each of the indicia 706-710 has a different number corresponding to a particular circumferential caliber. By way of example, gauge step 706A is of a particular color, represented in the drawing by dots and has a circumferential measurement of 39 millimeters. The corresponding measurement indicia for 706A is 706, which also features the same color, represented by dots. Gauge step 708A is of a distinctive color represented here by diagonal lines. The corresponding indicia 708 is also marked in the same color and is denoted by diagonal lines and has a circumferential measurement of 42 millimeters. The gauge step 710A is denoted by a color representing herein by cross-hatching. The corresponding indicia 710 is, likewise, shaded with the same color, represented by cross-hatching and has a circumferential measurement of 45 millimeters. An exemplary use of the illustrative sizing gauge in a surgical procedure is now described below.

Figure 8:
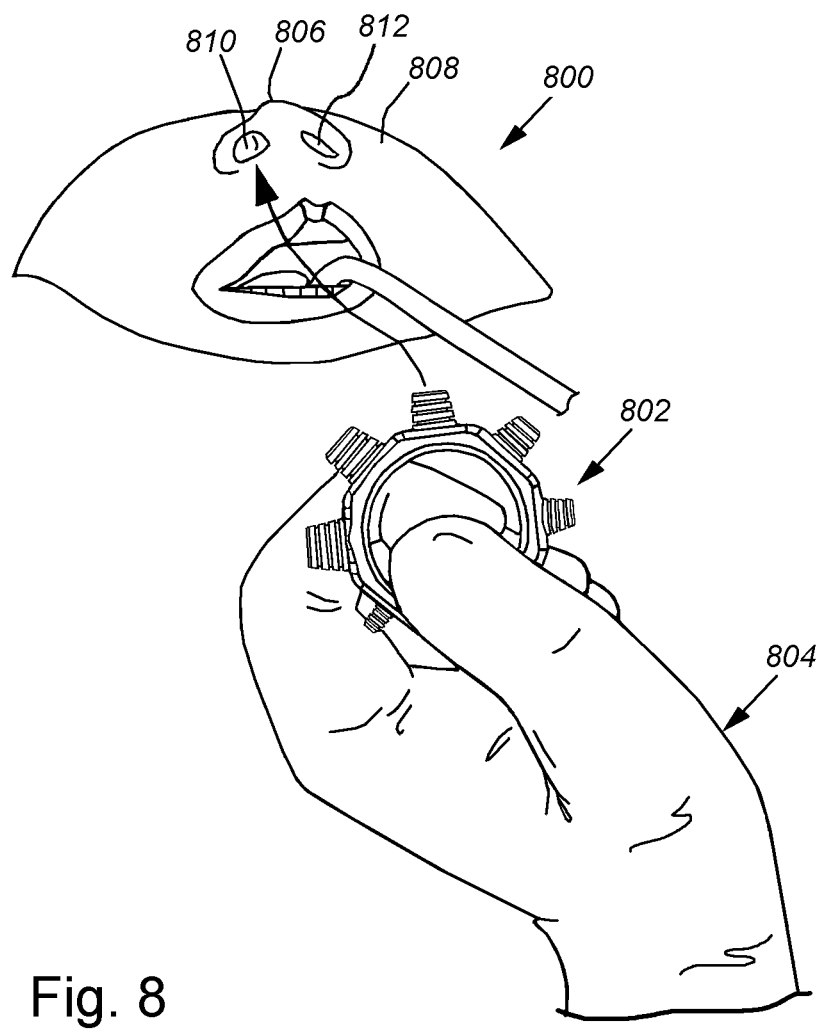
FIG. 8 is a frontal perspective of an illustrative patient about to undergo nostril gauging utilizing the illustrative nostril gauge in preparation for nasal reconstruction to correct post-cleft surgery deformity.

FIG. 8 is a view 800 of the illustrative sizing gauge 802 that is grasped in the hand of the cleft surgeon or other appropriate practitioner 804 in preparation to insert the gauge into the nose 806 of a patient 808 for the purpose of determining the caliber of each of the nostrils. The cleft surgeon 804 will insert the appropriately sized gauge spine of gauge 802 first into the normal nostril 810 and then into the abnormal nostril 812 and notes the difference between the relative.

Figure 9:
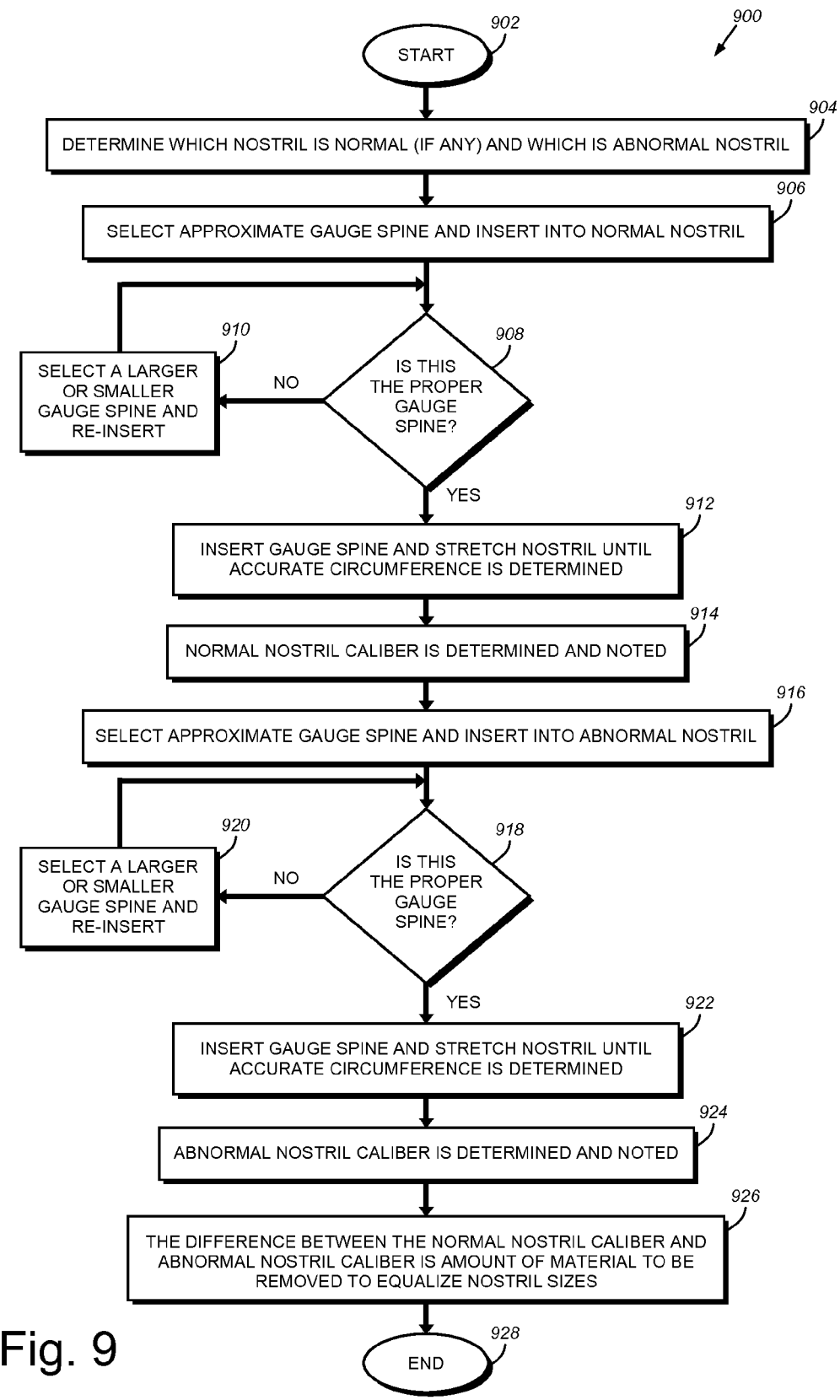
FIG. 9 is a flow chart that describes the procedure for gauging the nostrils utilizing the illustrative nostril gauge and determining the amount of material to be removed during nasal reconstruction in accordance with an overall medication treatment procedure therefor.

FIG. 9 is a flow chart that describes the procedure 900 for determining the relevant nostril calibers in detail. It is expressly contemplated that other medical treatment steps prior to and after those steps described above and in FIG. 9 can be implemented in accordance with conventional techniques. Such techniques are described in the background of the invention herein. The cleft surgeon commences the process (step 902) by visually inspecting the nose and determining which nostril is normal, if any, and which is abnormal (step 904). The surgeon then selects an approximate gauge spine that will be inserted first into the normal nostril 902. In step 908, the surgeon then determines whether this candidate gauge is correct in size 908 and if not, selects either a larger or smaller gauge spine and in step 910 reinserts as needed, defining a second through nth candidate diameter until the respective second through nth candidate diameter is correct. If the candidate gauge spine is correct in size, then the surgeon continues to insert the gauge spine and stretches the nostril until the accurate circumference is determined (step 912). Insertion of the nostril gauge into a nostril causes elastic deformation of that nostril and converts its shape from an irregular shaped form to a circular configuration. The surgeon then reads the gauge spine and observes which of these steps has fully expanded the nostril. In step 914, the surgeon then notes the corresponding caliber indicia and records that measurement. The surgeon then refers to the abnormal nostril and makes an estimation of the approximate gauge spine that correlates to that nostril and inserts the candidate gauge spine into the abnormal nostril (step 916). The surgeon then determines whether or not the candidate gauge spine is the correctly sized gauge spine for this nostril (step 918). If the gauge is too large or small, then the surgeon selects a larger or smaller size and reinserts the respective gauge spine (step 920), defining a second through nth candidate diameter until the respective second through nth candidate diameter is correct. Once the proper gauge spine is found, the surgeon stretches the nostril around the gauge spine until the accurate circumference is determined (step 922). The surgeon then refers to the appropriate gauge step and notes the corresponding indicia and records that measurement (step 924). The surgeon then determines the difference between the normal nostril caliber measurement and the caliber of the abnormal nostril and this difference instructs how many millimeters of material should be removed from the larger nostril in order to equalize the nostril sizes (step 926). The procedure 900 allows the surgeon to readily determine in an expeditious and accurate manner, the calibers of the relevant nostrils.

Figure 10:
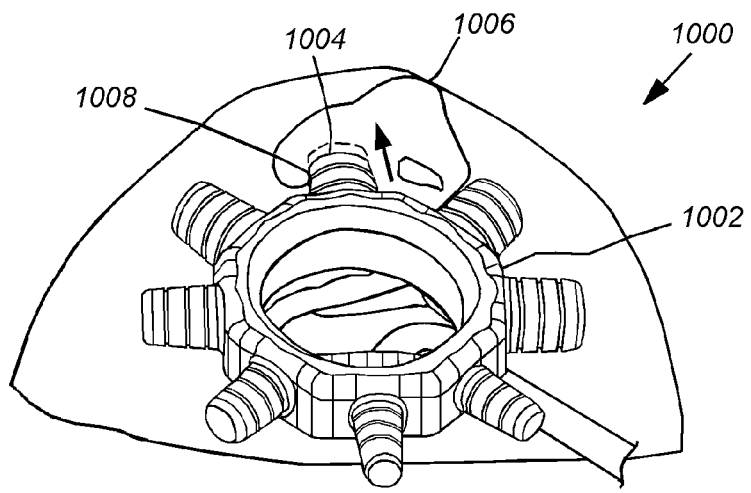
FIG. 10 is an off-center frontal perspective of a an illustrative patient during nostril gauging utilizing the illustrative nostril gauge and describing the elastic deformity of the gauged nostril.
Figure 11:
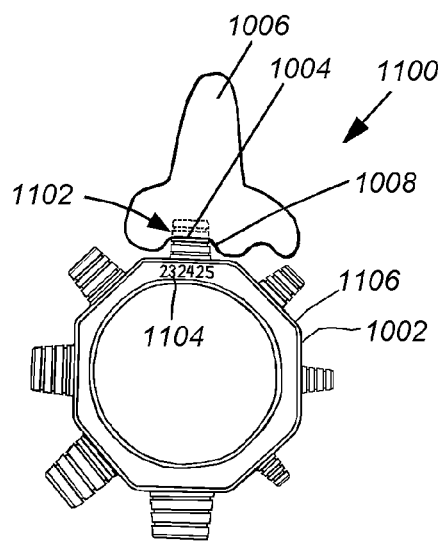
FIG. 11 is a frontal schematic of a an illustrative patient's nose during nostril gauging of the normal nostril depicting penetration of the gauge spine of the illustrative nostril gauge.
Figure 12:
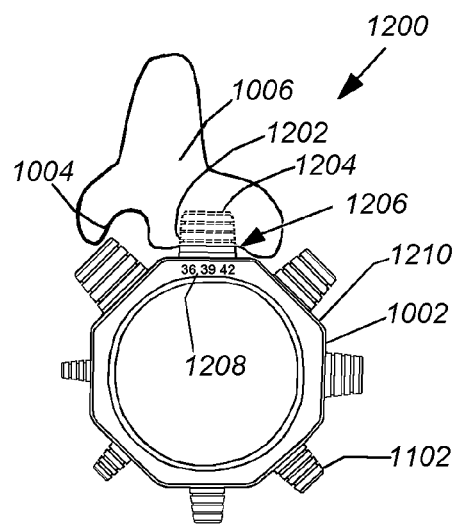
FIG. 12 is a frontal schematic of a an illustrative patient's nose during nostril gauging of the abnormal nostril depicting penetration of the gauge spine of the illustrative nostril gauge.

With further reference to FIGS. 10-12 the various steps of the procedure 900 above (FIG. 9) are graphically depicted. FIG. 10 is a frontal perspective view 1000 of the nostril gauge 1002 inserted into the normal nostril 1004 of a nose 1006. The gauge spine 1008 is inserted into nostril 1004 causing the nostril opening to stretch into a circle around the gauge spine 1008 (see for example step 906).

FIG. 11 is a simplified schematic view 1100 in which the illustrative nostril gauge 1002 is inserted into the normal nostril 1004 of the nose 1006. Gauge spine 1008 is inserted into the nostril 1102. In the exemplary procedure, the distal gauge step 1008 engages the nostril opening and is the correct gauge step. The respective indicia 1104 is "27" referring to a caliber of 27 millimeters in circumference (see step 912 above).

FIG. 12 is a schematic frontal view 1200 in which the nostril gauge 1002 has been inserted into the abnormally-sized nostril 1102 of the nose 1006. The illustrative gauge spine 1204 is inserted into the nostril until the accurate caliber is found and this corresponds to the proximal gauge step 1206 on gauge spine 1204 (see step 922 above). The cleft surgeon refers to the inscribed indicia 1208 of the nostril gauge body 1210 and notes the indicated number "42", which refers to a nostril circumference of 42 millimeters. The cleft surgeon in this example can then make a determination of the circumferential difference between the normal nostril 1004 and the abnormal nostril 1202. The difference in this example is found by the subtraction of the smaller nostril circumference, "27" from the larger circumference "42", resulting in a difference of 15 millimeters. This difference instructs the surgeon as to how much material to remove from the floor of the abnormal nostril 1202 in order to equalize the abnormal nostril circumference with the normal nostril circumference. The cleft surgeon then removes the 15 mm strip of material and proceeds to maneuver the nostrils and septum into their new orientation, after which, the nose is re-secured.

Once the nose has been secured, the cleft surgeon then re-measures each nostril with the nostril gauge, in the same manner as set forth above, in order to verify the accuracy of the reconstructive surgery. The cleft surgeon confirms that the nostrils have been equalized and the patient continues into recovery. If this final measurement reveals a difference, the cleft surgeon can re-adjust the nostrils as needed, re-measure and confirm a satisfactory result.

Figure 13:
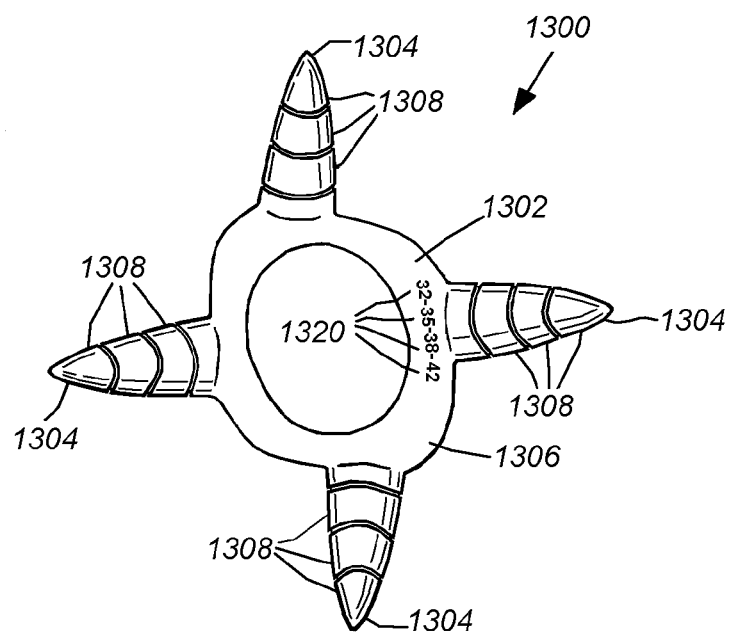
FIG. 13 is a frontal view showing a nostril gauge having four radially off-center gauge spines arranged with a center loop, according to an alternate embodiment.

FIG. 13 is another illustrative embodiment of the nostril gauge in which the nostril gauge 1302 has four gauge spines 1304 set around a loop body 1306 in an offset configuration that is offset relative to radii emanating from the base centroid. The reason for this offset configuration is to ease insertion. The illustrative four-spine offset nasal gauge 1302 has three gauge steps 1308 per gauge spine 1304. The increment between the gauge steps in this example is 2 millimeters and the range of calibers is between 20 and 42 millimeters in circumference. The gauge spines 1304 can be furnished with gauge steps 1308 that are more numerous and can result in finer differences in circumference between the steps as desired. The illustrative gauge can be provided with indicia 1320 that describe the sizes of the corresponding gauge steps.

An advantage to the embodiment of FIG. 13 is that there is more circumferential separation between the gauge spines than in the above-described octagonal embodiment. The use of fewer spines potentially reduces confusion and the risk of interference between the spines during measurement. The nostril gauge of FIG. 13 can be part of a set of a plurality of gauges in which each gauge represents a given size range. For example, one gauge with relatively fine size increments can be applicable to infants, another gauge can be appropriately sized for children, while another gauge can be provided for adults and adult-sized children. Likewise, specialty size gauges for large-nostriled patients can be provided. It is further contemplated that the shape and size of the gauge spines, as well as various indicia, can be similar to those described above with respect to the above-described embodiment.

Figure 14:
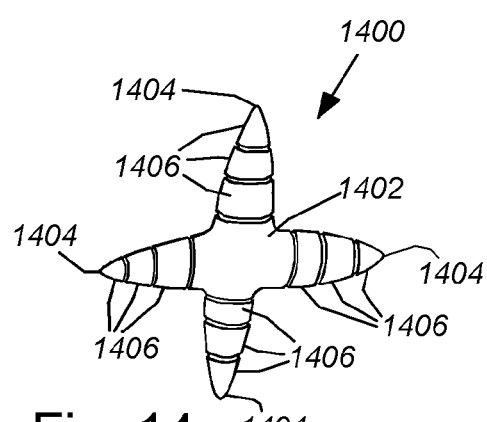
FIG. 14 is a frontal view showing a nostril gauge having four radially centered gauge spines with an intersecting base that is free of a central opening, according to an alternate embodiment.

FIG. 14 is an alternate embodiment 1400 of a four-pointed nostril gauge 1402 having four gauge spines 1404, each of which has three gauge steps 1406. The illustrative gauge 1402 is depicted with an intersecting base that is free of a central opening. Each of the exemplary gauge steps 1406 has a 2 millimeter increment in circumferential size. The illustrative nostril gauge 1402 can be furnished with more points to the extent that it is possible to insert the gauge spine 1404 into a nostril without having the insertion be obstructed by any of the other gauge spines. Also, while the illustrative gauge 1400 is shown with a base in which the crossing gauge spines emanate from a common center on a common plane, it is expressly contemplated that the double-ended spine members can be overlaid in parallel planes and joined at their crossing point. It is further contemplated that the shape and size of the gauge spines, as well as various indicia, can be similar to those described above with respect to the above-described embodiment. For the purposes of this embodiment, and other crossing shafts, the gauge body can be considered the region adjacent to the intersection between shafts that allow it to be held by the practitioner.

Figure 15:
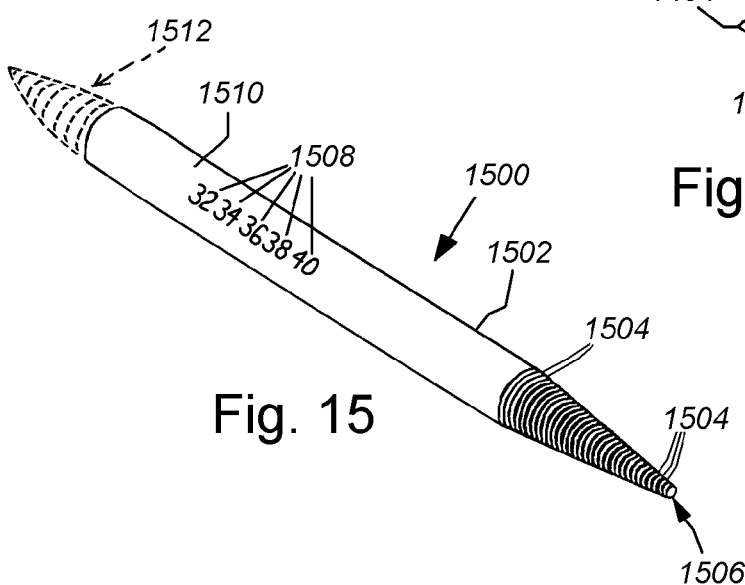
FIG. 15 is an off-center frontal perspective view showing a nostril gauge having a single gauge spine at the one or both ends, with the gauge steps in a series of diminishing circumferential steps as they approach the outer end, according to an alternate embodiment.

FIG. 15 is an alternate embodiment 1500 in which the body of the nostril gauge 1502 is in the form of a linear probe having concentric gauge steps 1504 at the distal end 1506. This form of a gauge will function in a manner similar to the urethral dilator found in the prior art, but can be furnished with indicia 1508 in the manner as set forth above inscribed upon the body 1510 of the nostril gauge 1502. Given the length of the gauge at the distal end 1506 and the utile function of inserting the gauge 1502 into a nostril, it may be desirable to provide a set of these nostril gauges in different sizes, for example, small, medium and large, to avoid over-penetration of the distal end 1506 when attempting to gauge larger nostrils. Likewise, the gauge steps can be provided at both ends, for example, at the end 1512, shown in phantom. Alternatively, the shape of the body 1502 can be non-linear, for example, defining a curve, rectilinear shape or an s-shape.

Figure 16:
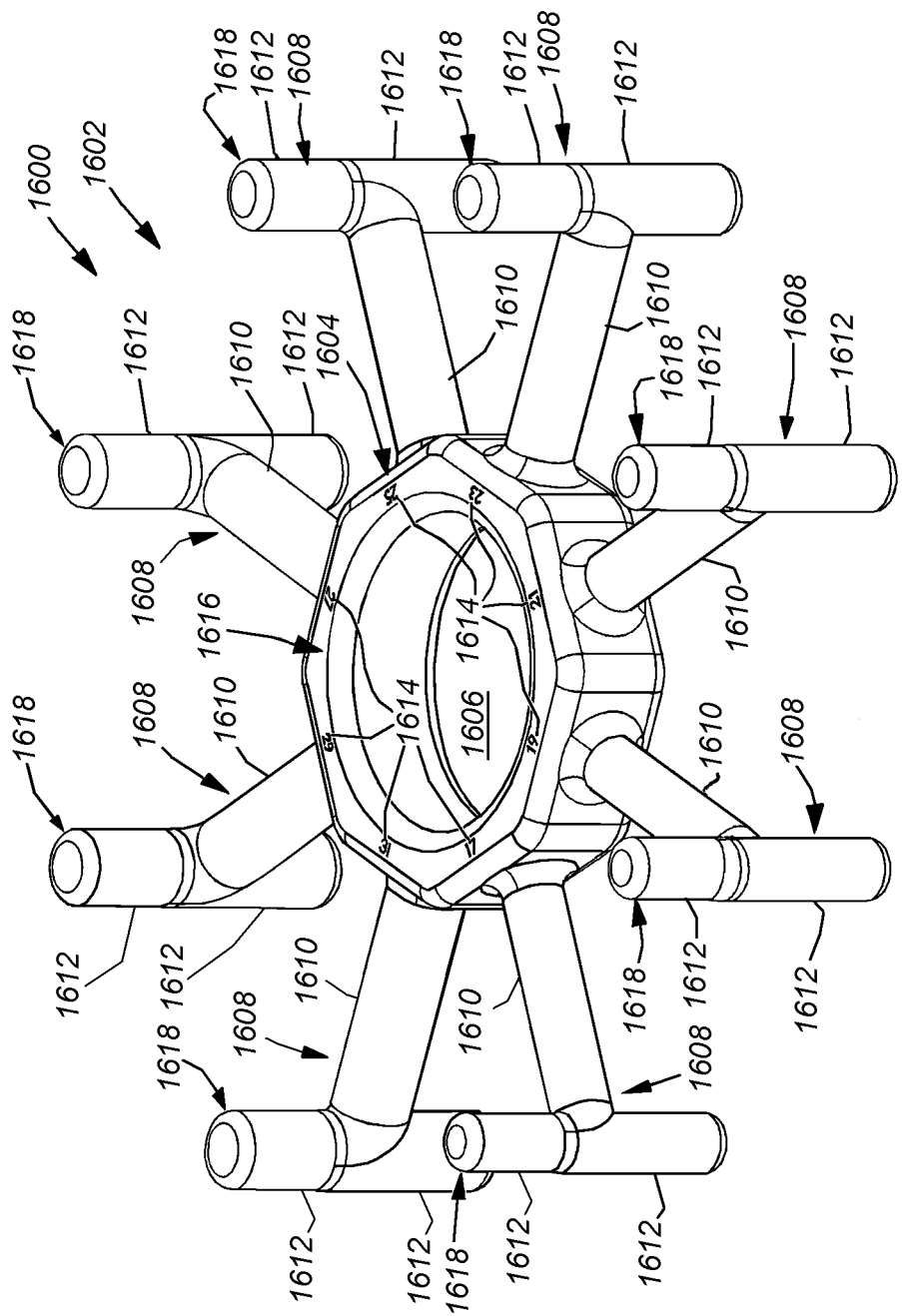
FIG. 16 is an off-center frontal perspective view showing a gauge having a cut-out center hole and eight radial incremental gauge arm assemblies, each of which is furnished with two gauge spines if different sizes, according to an alternate embodiment.

FIG. 16 is a perspective view of an alternate embodiment 1600 in which the body of the nostril gauge 1602 has an octagonal gauge body 1604 that has a center cutout hole 1606 which is provided to reduce the weight, as well as providing a gripping feature for the cleft surgeon. The center cutout hole is approximately 1 inch in its inner diameter. The illustrative nostril gauge is furnished with eight radial incremental gauge arm assemblies 1608. This embodiment provides a gauge in which each of the measuring gauges is spread apart from each other, such that they do not interfere with each other or interact with the patient during the measurement. The gauging process for this embodiment is the same as described in FIGS. 10-12 above. Each of the respective gauge arm assemblies 1608 is tee-shaped and is furnished with a gauge arm 1610 and two counter-posed gauge spines 1612. Each of the gauge spines 1612 is sized according to a different and discrete size increment. In other words, each spine's size is distinct from another gauge spine's size. In alternate embodiments, certain gauge spines in a given plurality of arms can be similarly sized. This can be desirable where a particular size of gauge spine is often used and it is convenient to place that size at more than one location on the overall nostril gauge. In another embodiment, some of the gauge arm assemblies can have counter-posed gauge spines while others can have one gauge spine. The diameters of the exemplary gauge arms are sized to match the diameter of the broadest nostril gauge spine mounted thereon. By making each of the arms relate in size to the relevant gauge, the mind is helped to index the gauge size because association with the particular size expedites the gauging process. In an alternate embodiment, the gauge arms are of a uniform diameter or sized relative to the narrowest nostril gauge mounted thereon.

The illustrative nostril gauge 1602 is furnished with size indicia 1614. In this embodiment, the size indicia 1616 and arranged on an outer face 1616 of the gauge body 1604. The size indicia are arranged so that there is at least one indicium for every related gauge size 1618. The indicia that correspond to the larger diameters are printed on the opposite side of the gauge in this illustrative embodiment. In alternate embodiments, the size indicia can be printed or embossed upon the gauge body or the respective gauge arms or corresponding gauge spines. The materials utilized to form the nostril gauge are those that are set forth in the description of FIG. 4 above. While this embodiment is depicted as having eight gauge arm assemblies, it is expressly contemplated that the nostril gauge can be provided with more or fewer gauge arm assemblies. It is further contemplated that an intermediate-sized gauge spine could be affixed so as to project from the end of the gauge arm coaxial to the gauge arm, to provide three sizing gauges on each gauge arm assembly.

Figure 17:
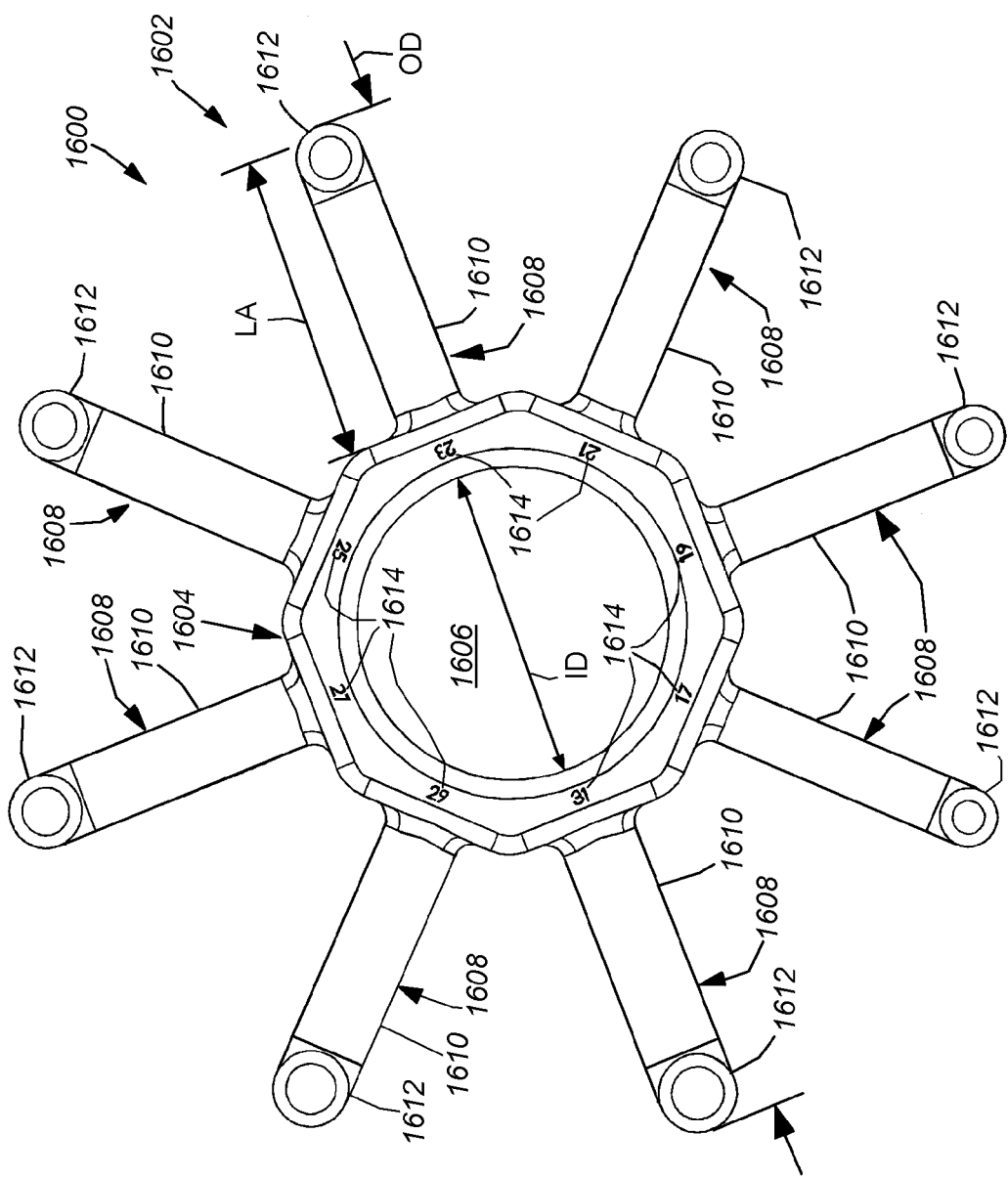
FIG. 17 is a side view of the illustrative embodiment of FIG. 16.

FIG. 17 is a top view of the illustrative nostril gauge of FIG. 16. The inner diameter ID of the center cutout hole 1606 is approximately one inch. In an alternate embodiment, the nostril gauge is provided without a center cutout hole. The length LA of each gauge arm assembly 1608 is approximately one inch. The overall diameter OD is approximately three and a half inches. It is expressly contemplated that these dimensions can be greater or lesser based on the user requirements. The gauge arm is depicted having a circular cross section but in alternate embodiments can have an ovular, rectangular, elliptical or a combination thereof.

Figure 18:
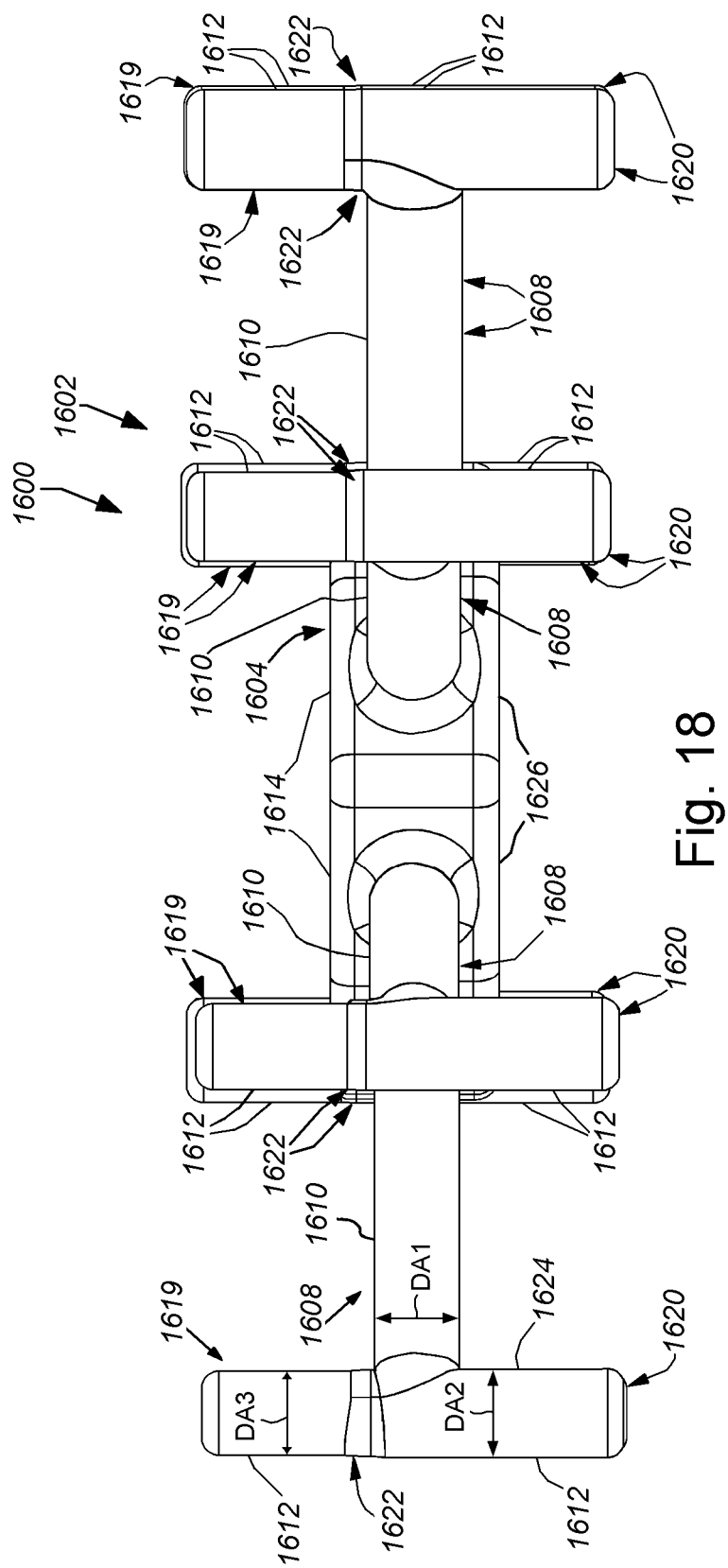
FIG. 18 is a top view of the illustrative embodiment of FIG. 16.

FIG. 18 is a side view of the illustrative nostril gauge of FIG. 16. The respective gauge arm assemblies 1608 are furnished with a smaller diameter gauge spine 1619 and a larger gauge spine 1620. The smaller diameter gauge spine 1619 is necked down at the frustum 1622. In the illustrative embodiment, the diameter DA1 of the gauge arm 1610 corresponds with the diameter DA2 of the related larger diameter gauge spine 1624. In an alternate embodiment, the diameter DA1 of the gauge arm 1610 corresponds with the diameter DA3 of the related smaller diameter gauge spine 1619. The size indicia 1614 relate to the respective smaller diameter gauge spine 1619 on one face of the gauge body 1604 and the size indicia 1626 relate to the respective larger diameter gauge spine 1624. In an alternate embodiment, the indicia can be color-coded or letter-coded instead of numbered. Likewise, the orthogonal (approximate right-angle between the axis of the spine and that of the gauge arm) orientation allows for mounting of a larger number of gauge spines with desirable spacing therebetween, including full length spines on both sides of each arm. Note that in an alternate embodiment, the depicted tee-shape (with two counterpoised gauge spines per gauge arm) can be substituted with an L-shape having a gauge spine on one side of the arm only. In this embodiment, the axis of each spine is parallel to the respective axis of each of the other spines.

In operation the nostril gauge 1602 can be used effectively by the surgeon to gauge a nostril size. The ergonomic properties of the gauge facilitate its use without the adjacent arms interfering with the patient's nostril or the gauging process. The operator's hand can be held at a more natural and ergonomic posture due to the orthogonal orientation of the gauge spines on the gauge arms. The angular spacing between gauge arms about the perimeter of the gauge body is also highly variable. In an illustrative embodiment, the arms are spaced at an even angular spacing about the perimeter—in this example, eight arms each spaced by 45 degrees with respect to adjacent arms, and all residing in a common plane that includes the body. In alternate embodiments, the angular spacing can vary, with some arms closer together than other arms—for example, where more clearance is needed between spines, the spacing can be increased. Likewise, the length of individual arms can be approximately equal, as shown, or can be different from each other as appropriate to enhance ergonomics and/or provide needed clearance. The body, while having an outer perimeter in the shape of an octagon, with each arm mounted along a side thereof, can be any acceptable regular or irregular shape (circle, oval, polygon, etc.).

Also, the gauge can be constructed as a unitary member (using molding or other techniques, or it can be constructed from separate components that are mechanically, thermally and/or adhesively joined together. The components can be constructed from the same material or a combination of materials. For example, the body can be polymer or composite, while the spines are metal. Any biocompatible metal, polymer, ceramic or composite can be employed to construct any of the gauge components. The gauge of this embodiment (or any other embodiment herein) can be constructed as an injection molded, unitary part from a variety of polymers. In an embodiment, polycarbonate can be employed for all or a portion (i.e. using co-molding techniques with multiple materials) of the gauge. In alternate embodiments a somewhat flexible material, such as polycarbonate-urethane can be used to construct (at least) the gauge arms, thereby providing inherent elastic-deformability (flexibility) to the arms. This can be desirable in assisting the practitioner in flexing unused gauge spines/arms away from (free of) any interference with the arm/spine that is in use during a procedure.

It should be clear that the various embodiments of a nostril gauge described herein allow the practitioner to employ (typically) a single, reusable device to accurately and efficiently determine nostril size preoperatively, during the procedure and post-operatively. The practitioner is generally freed from the need to pick up a number of loose devices, having the entire given size range simultaneously at his or her fingertips.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. In general, the description herein should be taken broadly to encompass devices employed to facilitate the accurate gauging of the size/caliber of deformed nostrils resulting from any cause such as from a cleft lip and/or cleft palate, a traumatic injury, an infectious process, a prior surgical intervention, etc. The illustrative device described herein generally allows for the expeditious and accurate measurement of the size/caliber of normal and deformed nostrils before any type of nasal reconstruction intended to correct asymmetric nostril openings (nares). By way of further example, while the illustrative embodiments refer to the use of the gauge in nasal reconstructions resulting from a cleft lip and/or palette, the application of the illustrative gauge can be broader—such as use in general nasal reconstructive surgery. More particularly, appropriately sized and arranged embodiments of the illustrative gauge can be adapted for use in general reconstructive surgical procedures requiring a measurement of an orifice. Thus, while the terms "nasal" or "nostril" are used herein, it is expressly contemplated that, where not otherwise specifically limited to a nasal application, the gauge can adapted to the appropriate non-nasal function within the teachings of the embodiments. Additionally, while indicia are shown on gauge steps (in the forms of colors, etc., and are correlated to sizes on an adjacent readable location, such as the gauge body, it is contemplated that basic number indicia can be provided on an adjacent location to each spine. The number indicia can correlate to each step in that spine. Accordingly, this description is meant to be taken only by way of example, and not to otherwise limit the scope of this invention.

What is claimed is:

1. A gauge for determining a perimeter dimension of an orifice in a body comprising:
    a gauge body constructed and arranged to allow grasping by a user; and
    a plurality of gauge spines spacedly mounted about a perimeter of the gauge body, each of the gauge spines including a plurality of frustoconical gauge steps arranged proximally-to-distally radially with respect to a center of the gauge body, in successively smaller diameters, the plurality of gauge spines including at least one discontinuity between at least two of the plurality of frustoconical gauge steps, at least one of the spines including at least one gauge step differing in diameter from the gauge steps of another of the spines.

2. The gauge as set forth in claim 1 wherein the gauge body comprises a ring having an open center.

3. The gauge as set forth in claim 1 further comprising indicia associated with at least some of the gauge steps each defining the diameter of one of the steps.

4. The gauge as set forth in claim 1 wherein the body orifice is a nostril and the diameter of each of the gauge steps defines a diameter of a nostril of predetermined inner perimeter size.

5. A gauge for determining a perimeter dimension of an orifice in a body comprising:
    a gauge body constructed and arranged to allow grasping by a user; and
    a plurality of gauge arms mounted about a perimeter of the gauge body and defining a single plane extending through each of the plurality of gauge arms, each of the gauge arms having interconnected therewith at least one of a plurality of gauge spines, the gauge spines being constructed and arranged to engage the orifice with a diameter, at least some of the gauge spines differing in diameter from others of the gauge spines,
    wherein at least some of the gauge arms include a pair of the gauge spines arranged in a counterposed relationship with respect to each other and extending along an axis orthogonal to the single plane, and extending in opposing directions with respect to the single plane.

6. The gauge as set forth in claim 5 wherein the gauge body includes an open center for grasping.

7. The gauge as set forth in claim 5 further comprising indicia located with respect to at least some of the gauge spines indicating the diameter of the respective of the gauge spines.

8. The gauge as set forth in claim 5 wherein the pair of gauge spines extend along the axis at a right angle with respect to the single plane.

9. The gauge as set forth in claim 8 wherein the axis of the pair of gauge spines is parallel to an axis of at least others of the gauge spines.

10. The gauge as set forth in claim 9 wherein the gauge arms reside substantially within the single plane and the arms are a mounted about a perimeter of the gauge body at approximately equal angular spacings therebetween.

11. The gauge as set forth in claim 5 wherein at least some of the gauge arms are constructed from a flexible material so that the gauge arms constructed from the flexible material can be elastically deformed away from a predetermined of the gauge spines so as to be free of interference therewith during use.

\* \* \* \* \*